(12) United States Patent
Roisin et al.

(10) Patent No.: US 7,208,266 B2
(45) Date of Patent: Apr. 24, 2007

(54) ENDOGENOUS COAGULATION ACTIVATOR COMPOUNDS —USE IN EXPLORING ENDOGENOUS COAGULATION

(75) Inventors: Jean-Paul Roisin, Saint-Maur des Fosses (FR); Stéphane Steurs, Franconville (FR); Gérard Quentin, Yevres (FR)

(73) Assignee: Societe Diagnostica-Stago (FR)

( * ) Notice: Subject to any disclaimer, the term of this patent is extended or adjusted under 35 U.S.C. 154(b) by 268 days.

(21) Appl. No.: 10/302,649

(22) Filed: Nov. 22, 2002

(65) Prior Publication Data
US 2003/0157582 A1   Aug. 21, 2003

Related U.S. Application Data

(63) Continuation of application No. PCT/FR02/01020, filed on Mar. 22, 2002.

(30) Foreign Application Priority Data
Mar. 23, 2001  (FR) .................................. 01 03979

(51) Int. Cl.
C12Q 1/00  (2006.01)
G01N 33/86  (2006.01)

(52) U.S. Cl. ........................................... 435/4; 436/69

(58) Field of Classification Search .................... None
See application file for complete search history.

(56) References Cited

U.S. PATENT DOCUMENTS 4,797,471 A   1/1989  Teetz et al.
4,994,192 A   2/1991  Corin et al.

FOREIGN PATENT DOCUMENTS

| DE | 2750560 A1 | 5/1978 |
|---|---|---|
| EP | 0228625 A2 | 12/1986 |
| EP | 0241314 A2 | 10/1987 |
| EP | 0 525035 B1 | 2/1993 |
| FR | 2370705 | 6/1978 |
| JP | 60 199850 | 10/1985 |

OTHER PUBLICATIONS

Krogh et al., "Structure-activity relationships for the analgesic activity of gallic acid derivatives", Il Farmaco 55 :730-735 (2000).*
Howard H. Weetall, Enzymatic Synthesis of Gallic Acid Esters, vol. 11 Applied Biochem. & Biotech., pp. 25-28 (1985).

* cited by examiner

*Primary Examiner*—Sandra E. Saucier
(74) *Attorney, Agent, or Firm*—Lerner, David, Littenberg, Krumholz & Mentlik, LLP

(57) ABSTRACT

The invention concerns contact activators for the endogenous coagulation pathway and their use in exploring coagulation anomalies.

The activators of the invention are derivatives of gallic acid, preferably polyethylene glycol gallates.

17 Claims, 1 Drawing Sheet

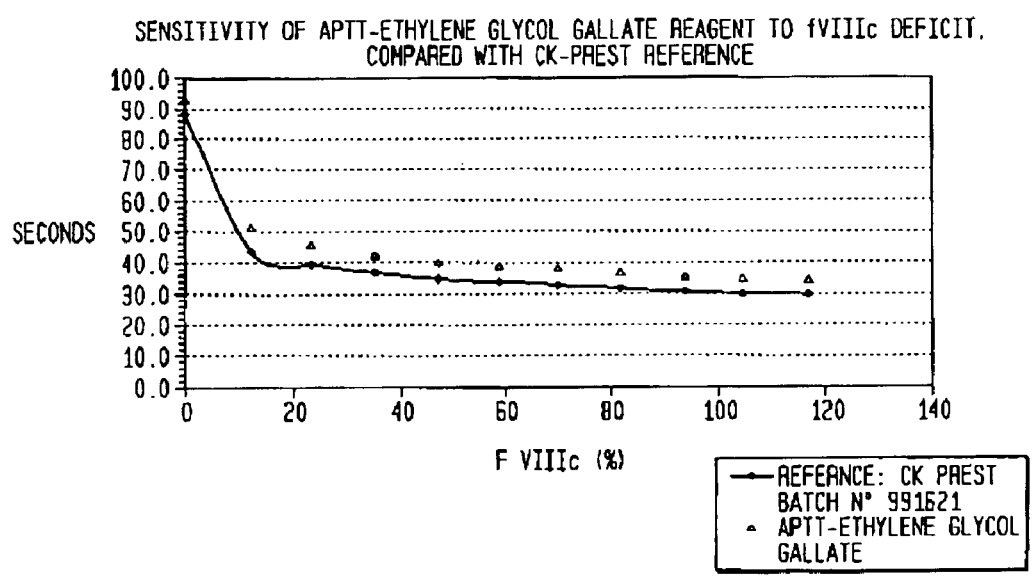

ENDOGENOUS COAGULATION ACTIVATOR COMPOUNDS —USE IN EXPLORING ENDOGENOUS COAGULATION

This application is a continuation of international application no. PCT/FR 02/01020, filed Mar. 22, 2002, published in French, which claims priority from French application no. 0103979, filed Mar. 23, 2001.

The present application relates to activator compounds for endogenous coagulation and to their use for its exploration.

Coagulation initiated by the "endogenous pathway" results in vitro from exposing blood to contact with a negatively charged surface. In vivo, it provides secondary reinforcement of the growth of the fibrin clot.

Exploration of coagulation initiated by the "endogenous pathway" (hereinafter designated by the expression "endogenous coagulation") is used in tests for in vitro detection of coagulation anomalies or to monitor patients treated with substances with an anti-coagulating activity.

The endogenous coagulation pathway is initiated in vitro by activation of factor XII (f.XII) in contact with negative charges. In the presence of other enzymatic factors such as factor XI (f.XI), prekallikrein (PK), high molecular weight kininogens (HMWK), factor IX is (f.IX) also known as anti-haemophilic factor B, and a co-factor, anti-haemophilic factor A (f.VIIIc), a cascade of activation of an enzymatic type is triggered in the simultaneous presence of platelet phospholipids (PF3) and of calcium (Ca$^{++}$).

At the end of that series of activations, the activated factor IX (f.IX) in its turn triggers cascade activation of a second series of enzymes including factor X (f.X), and factor II (f.II) also known as prothrombin; that activation is accomplished in the presence of a platelet factor (PF3), calcium (C$^{++}$) and a co-factor, factor V (f.V).

The second activation cascade ends in the formation of thrombin (f.IIa), which transforms fibrinogen into fibrin, a major constituent of the blood or plasma clot.

The simplified scheme for the endogenous (in vitro) coagulation pathway can be illustrated as follows:

anomalies affecting fibrin formation resulting from the transformation of fibrinogen by thrombin.

Different tests are commercially available to explore endogenous coagulation (also known as intrinsic coagulation) and in particular, the activated partial thromboplastin time test, APTT, can be mentioned, which can detect anomalies or deficits in a plasma sample at the level of factors involved in the endogenous pathway, which anomalies are shown up by coagulation times that are outside normal limits.

The APTT test is carried out to discern the most frequent constitutional haemorrhagic diseases, namely Willebrand's disease and haemophilia A and B. That test is also frequently used to monitor heparin therapy.

Schematically, the principle of an APTT test consists of adding a negatively charged factor XII activator (contact activator) to the test plasma sample and a substitute for the phospholipids of the platelet membrane, along with calcium ions.

The measured coagulation time corresponds to the period between adding the contact activator, the platelet substitute, the calcium, and appearance of the coagulum. It is the time required to transform 1% of the prothrombin in the plasma into thrombin. Fibrin formation then occurs over a short period. Calcium is the triggering element for the system.

Activators suitable for carrying out APTT tests are relatively numerous. They include, for example, solid activators such as silica, glass or kaolin, or liquid activators such as ellagic acid and its derivatives, or sulphatides.

While reagents based on solid activators are widely used, they are not without certain disadvantages. The particles of kaolin or silica they contain tend to settle out during the coagulation test. Thus, continuous stirring must be provided, resulting in problems concerning the instability of the reagents and difficulties in carrying out the tests in automated instruments. Further, activators such as kaolin cannot be used to carry out optical coagulation measurements.

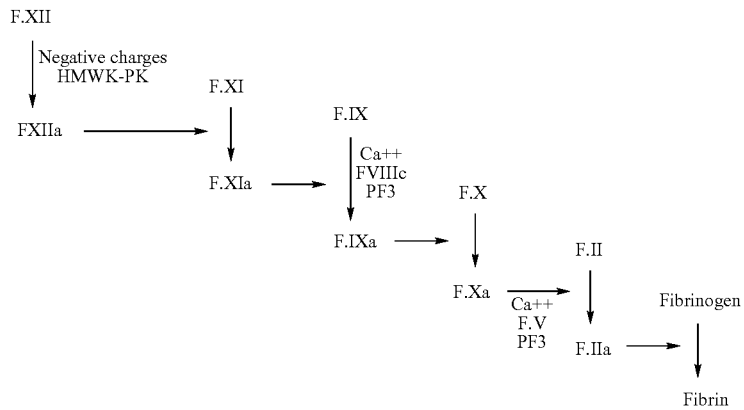

In general, coagulation exploration is carried out to look for a biological anomaly in a patient that may participate in a haemorrhagic syndrome or to monitor the consequences of a disease at the coagulation level, or to monitor medical treatment that may directly or indirectly modify coagulation.

To this end, different tests have been proposed to research, from qualitative or quantitative observation of factors involved in the endogenous coagulation pathway, different Liquid activators are an alternative to solid activators. However, activators such as ellagic acid are known to be susceptible of inducing variations in the test results. Further, their sensitivity is reduced compared with that of the preceding reagents. A variety of associations have been proposed to improve the performances of such reagents. As an example, International patent application WO-A-91/16453 recommends a reagent based on ellagic acid, phenol and a metal ion, preferably associated with dextran sulphate.

Other contact activators in solution have been described, in particular in European patent EP-A-0 525 035 in which the contact activator is a hydroxy-substituted aromatic compound selected from propyl gallate and tannin, in International patent application WO-A-98/44352, in which the contact activator is ellagic acid, and in United States patent U.S. Pat. No. 5,550,028, in which the contact activator is tetrahydroxy-1,4-quinone.

Sulphatides have also been proposed as activator compounds for coagulation via the intrinsic pathway. However, their activity level has not always been considered to be sufficient, and such compounds suffer from the further disadvantage of being relatively expensive compared with other available activators.

Thus, there is a need for novel coagulation reagents or to improve existing reagents to provide products that, while remaining advantageous from an economic viewpoint, have sufficient stability and sensitivity, induce a short activation time and can be used in automated analytical instruments in order to mass produce the tests.

The invention pertains to such alternative contact activators that are capable of participating in endogenous coagulation and in producing systems and tests that can explore this endogenous coagulation and enable anomalies to be detected.

The invention further relates to the use of these activators in an assay for the exploration of the endogenous coagulation, of the APTT type.

According to a particular embodiment, the activator of the endogenous coagulation is associated with compounds which allow modulation the sensitivity of the response of a reagent used in APTT, with respect to some anomalies of the coagulation time faced in certain pathologies.

In the context of their research into substances that can activate endogenous coagulation, the inventors have studied compounds with advantageous solubility properties compared with currently used compounds as coagulation activators in APTT tests and in particular starting from gallic acid, they have studied derivatives that are capable of activating endogenous coagulation.

In a field which is not related to the field of the invention, patent application DE 27 50 560 A1, describes esters obtained by esterification of gallic acid with ethylene glycol or with various polyethylene glycols. These esters are used as a protective material for glass fibers included in a composite material containing concret.

In another field, the field of antioxydant compounds for use against deterioration of fats and oils in food. Weetall H. H (Applied Biochemistry and Biotechnology vol 11, 1985) propose to synthesize esters from gallic acid, in using particular alcohols and diols. The publication specifies that, if esters and diol esters have indeed been synthesized using tannase from *Aspergillus niger*, the specific nature of the products remain to be determined.

The reagents in question are contact activators for the endogenous coagulation pathway, capable of having a pro-coagulating activity, i.e., of activating factor XII to activated factor XIIa, after incubating a plasma sample at 37° C. in the presence of PF3 and calcium.

Preferably, these compounds are soluble or can be rendered soluble, if necessary after modification.

Thus, the invention provides a compound with formula:

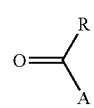

(I)

in which:

A is selected from the following formulae:

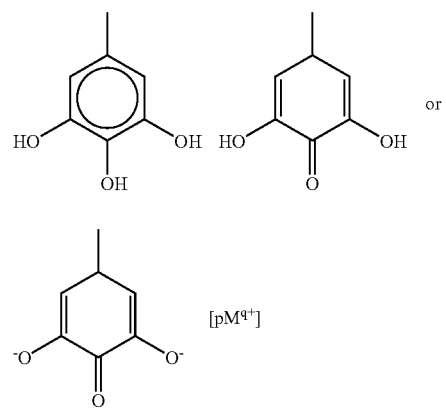

$M^{q+}$ representing a cation, q being equal to 1 or 2 and p being such that p×q=2;

R represents $$-\!\!\!\!+\!\!O\!-\!\!(CH_2)_m\!\!\rightarrow\!\!_n OH, \quad \text{or} \quad -\!\!\!\!+\!\!NH\!-\!\!(CH_2)_m\!\!\rightarrow\!\!_n NH_2,$$

m being equal to 2, 3, 4 or 5 and n being a whole number between 1 and 170; or $$-AA_1-AA_2-\ldots-AA_r,$$

AA being a natural or exotic amino acid and r being a whole number between 1 and 10.

Of the compounds defined above, in a particular embodiment, the invention concerns those compounds that have the advantage of being capable of being dissolved, in particular in an aqueous solution. Preferably, they are completely soluble.

The side chain constituted by R the meaning of which was given above is such that the value of n is preferably between 1 or more and 170 or less. In particular, n is in the range 1 to 50, for example in the range 1 to 30, advantageously in the range 1 to 20.

Particularly preferably, n is equal to 1, 2, 3, 4, 5, 6, 7, 8, 9 or 10.

A first family of preferred compounds in accordance with the invention is defined as follows:

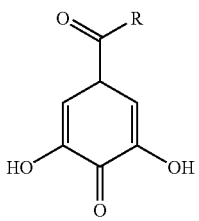
(II)

in which:

R represents

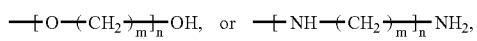

m being equal to 2, 3, 4 or 5 and n being a whole number between 1 and 170; or $-AA_1-AA_2-\ldots -AA_r$ AA being a natural or exotic amino acid and r being a whole number between 1 and 10.

In a first preferred embodiment of the invention, in one of formulae (I) or (II) above, R represents:

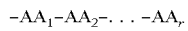

m and n having the meanings given above.

Advantageously, in the context of the invention, the compound with formula (II) is such that:

R represents $-[-O-CH_2-CH_2-]_n-OH$ where n is a whole number between 1 and 170, preferably between 1 and 10.

This preferred form of compound (II) of the invention corresponds to the oxidised form of polyethylene glycol gallates.

This oxidised form is the quinone form resulting from oxidation in an alkaline medium of one of the —OH groups of the aromatic ring present in formula (II).

In a further aspect, the compounds of the invention can also be constituted by a family with the following formula corresponding to an ionised form of formula (III), associated with mono- or divalent cations defined in the context of the invention:

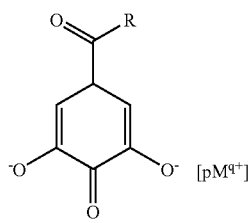
(III)

in which:

R represents:

m equals 2, 3, 4, or 5; and n is a whole number between 1 and 170; and $M^{q+}$ is a cation in which q is equal to 1 or 2 and p is such that p×q=2.

In addition to the quinone in the 4-position, this second particular family of compounds of the invention with formula (III) comprises the two —OH functions (in the 3- and 5-positions) in the ionised form (sodium alcoholate) formed when the pH of the medium is greater than the pKa.

In particular, the invention concerns the gallate of oxidised mono- or polyethylene glycol in its basic form, said compound being associated with cations, in an alkaline medium.

Preferably, it is the basic form of ethylene glycol gallate in which R has the meaning given above and m=2 and n=1.

This basic form of oxidised ethylene gallate is water-soluble.

To be capable of use, the pH of the composition obtained must be reduced to a physiologically acceptable value. Displacement of the equilibrium towards the sodium form of the quinone (according to formula III) at a physiological pH can be accelerated and stabilised by adding cations that endow it with immediate coagulating properties.

Of the compounds with formula (I) identified above, the invention advantageously provides compounds defined as follows:

(I)

in which:

A is:

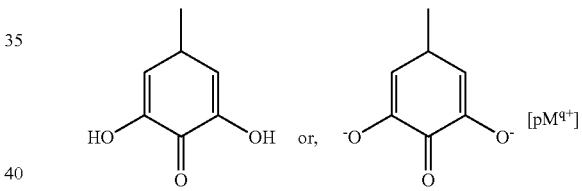

R is —O—CH$_2$—CH$_2$—OH;

$M^{q+}$ being a cation, q being equal to 1 or 2 and p being such that p×q=2.

These compounds are respectively the acid form of oxidised ethylene gluycol gallate and the basic or salt form of oxidised ethylene glycol gallate.

The basic quinone salt form is characterized by a yellow colour detectable at a wavelength of 355 nm and is particularly advantageous due to its solubility in aqueous media.

To produce the compounds of the invention as defined above and in the following pages, cation $M^{q+}$ is advantageously a metal cation, in particular $Mn^{2+}$ or $Cu^{2+}$ or $Co^{2+}$.

Alternatively, it can be constituted by a non-metallic cation, such as a counter-ion, which is supplied during preparation of the compound of the invention by heating in an alkaline medium. Such a preparation process is defined in the following pages and $M^{q+}$ is advantageously $Na^+$, $K^+$ or $NH_4^+$.

The concentration of cation can be defined as a function of the coagulation time to be observed for a normal reference sample. Advantageously for metal cations, this concentration is in the range 5 micromoles (μM) to 15 μM, preferably about 10 μM.

In a further particular embodiment, the invention provides a family of compounds with formula (I):

in which:
A is selected from the following formulae:

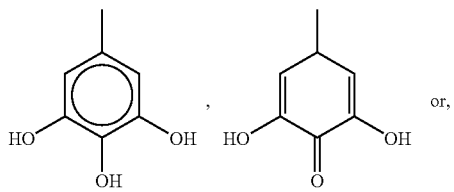

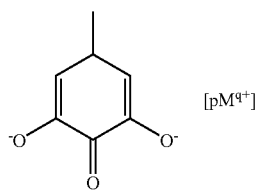

where $M^{q+}$ represents a cation, q being equal to 1 or 2 and p being such that $p \times q = 2$;

R represents $-[-NH-CH_2-CH_2-]_n-NH_2$ where n is a whole number between 1 and 170.

In particular, in the context of the definition of R, n is in the range 1 to 50, for example in the range 1 to 30, advantageously between 1 and 20.

A preferred form of polyethylene diamine gallate is the quinone form resulting from oxidising one of the —OH groups on the aromatic ring. It corresponds to the following formula:

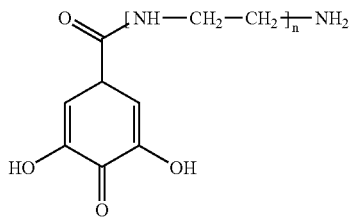

in which n is a whole number between 1 and 170; preferably it is in the range 1 to 50, for example in the range 1 to 30, advantageously in the range 1 to 20.

In the above formulae, n is particularly preferably equal to 1, 2, 3, 4, 5, 6, 7, 8, 9 or 10.

Advantageously, it is ethylene diamine gallate (n=1).

The compounds of the invention can also be in the form that is associated with mono- or divalent cations, in particular metal cations. These compounds have the following formula:

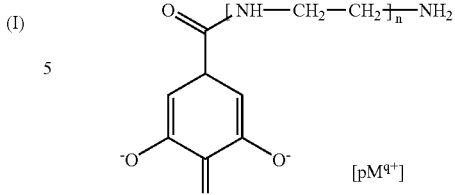

in which n is a whole number between 1 and 170;
$M^{q+}$ is a cation, q is equal to 1 or 2 and p is such that $p \times q = 2$.

In particular, n is in the range 1 to 50, for example in the range 1 to 30, advantageously in the range 1 to 20.

Particularly preferably, n is equal to 1, 2, 3, 4, 5, 6, 7, 8, 9 or 10.

In a third embodiment, the invention provides a compound characterized in that it has formula (I):

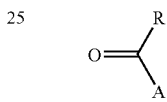

in which:
A is selected from the following formulae:

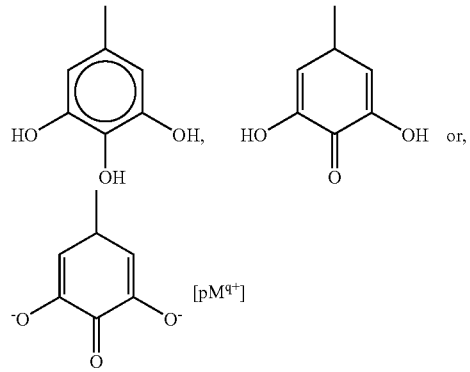

where $M^{q+}$ represents a cation, q being equal to 1 or 2 and p being such that $p \times q = 2$;

R is an amino acid residue or a peptide.

Preferably, as indicated in the case of the first two embodiments of the invention, the compounds of the invention are in the quinone form resulting from oxidation of one of the —OH groups on the aromatic ring:

A =
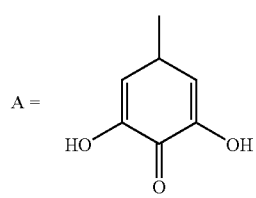

or in the form that is associated with mono- or divalent cations:

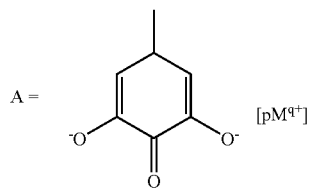

in which M, q and p have the definitions given above.

A preferred amino acid for producing the above compounds is serine in which:

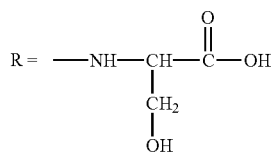

In this case, the compound of the invention advantageously has the following formula:

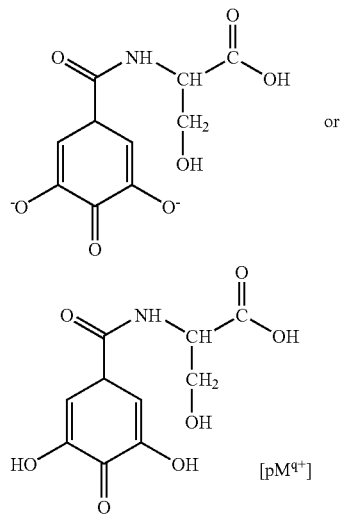

M, q and p having the meanings given above.

The invention also provides a composition characterized in that it comprises a mixture of a plurality of compounds, in particular a mixture of at least two compounds selected from those identified above, whether compounds from the same family or the same group or, in contrast, compounds belonging to different families or groups from those defined above.

In particular, a composition is characterized in that it comprises at least two different compounds with formula:

(I)

these compounds being identical or different for group A and being identical or different for group R, A and R having the meanings given above.

The invention preferably concerns a composition characterized in that it comprises a mixture of compounds (IV) and (V), respectively constituting the acidic and basic forms of oxidised ethylene glycol gallate (EGGox) with the following formulae:

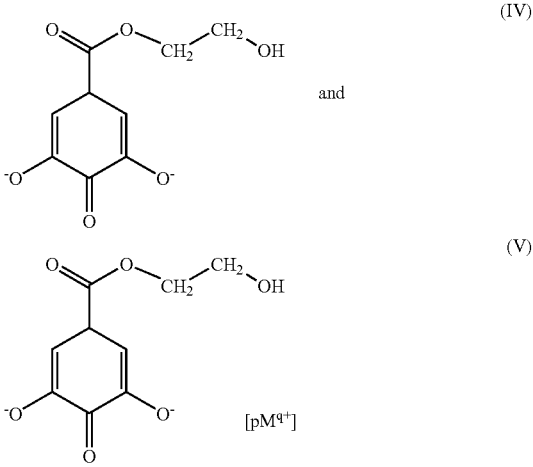

M, q and p having the definitions indicated above.

Thus, this composition comprises a mixture of acidic and basic forms of oxidised ethylene glycol gallate, corresponding to the products of the keto-enol equilibrium obtained from ethylene glycol gallate when it is either heated in an alkaline medium, or brought into the presence of metal cations.

The equilibrium between the acidic and basic forms of oxidised ethylene glycol gallate can be displaced towards one or other of these forms by adjusting the reaction conditions, in particular by modifying the pH or the concentration of cations present in the reaction medium.

Advantageously, the composition as defined is characterized in that it is a solution, preferably an aqueous solution.

In a particular aspect, within the context of the preceding definition, the invention concerns a composition in which the basic form with formula (V), oxidised ethylene glycol gallate, is predominant.

This water-soluble basic form has wholly advantageous properties as regards constituting an activating composition for endogenous coagulation, in particular for carrying out an in vitro test for exploring endogenous coagulation.

In a particular embodiment of the invention, the composition with one of the above definitions has a physiologically acceptable alkaline pH. This pH is adjusted after oxidising the EGG, for example in the presence of buffer Molecules: MOPS ((N-morpholino)propanesulphonic acid) or TRICINE (N-tris(hydroxymethyl)methyl-glycine). Advantageously, the MOPS molecule is selected.

In a further embodiment of the invention, the composition is characterized in that it comprises a mixture of different forms of the gallate, produced by the keto-enol equilibrium and with formula:

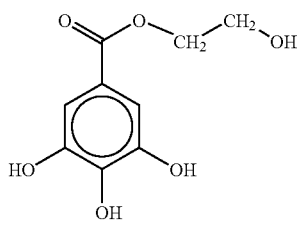 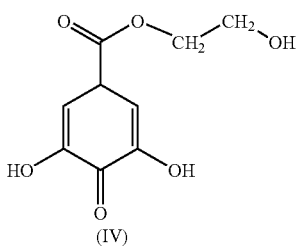 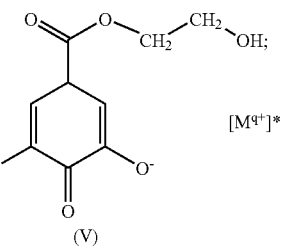

(IV) (V)

M, q and p have one of the definitions given above.

The presence of one or other of the forms of the enolate of the gallic acid ester is dependent on the reaction conditions, and the keto-enol equilibrium can thus be displaced to obtain a greater or lesser quantity of one of the gallate forms produced.

Within the context of the invention, there is a tendency to favour the presence of the basic form of the oxidised gallate, with formula (V).

Preferred compounds and compositions of the invention can also be defined as the result of carrying out a process comprising the following steps:
  esterifying gallic acid with ethylene glycol and recovering one of the reaction products constituted by ethylene glycol gallate (EGG) with the following formula:

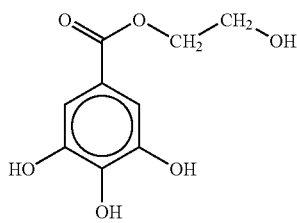

displacing the keto-enol equilibrium by bringing EGG into contact with an alkaline medium and heating to a temperature in the range 70° C. to 90° C.

The keto-enol equilibrium formation reaction is advantageously carried out for a period of 24 hours at 80° C.

Preparation using the above process results in a mixture of the 3 gallate forms, said mixture possibly being displaced towards the oxidised forms.

Preferably, the composition obtained is characterized in that the process further comprises the steps of:
  stabilising the keto-enol equilibrium obtained by adjusting the pH;
  recovering compounds with formula (IV) and (V) in solution, at an alkaline pH.

The oxidised forms of the EGG are formed in the presence of sodium hydroxide, in particular excess sodium hydroxide, to displace the keto-enol equilibrium towards the basic form of the oxidised ethylene glycol gallate. Heat treatment is carried out at a temperature in the range 70° C. to 90° C., preferably a temperature of 80° C. for a period of 24 hours.

The pH of the solution is an alkaline pH, and the action of the sodium hydroxide can be stopped by adding a buffer that contributes to stabilising the keto-enol equilibrium obtained. Particularly preferably, the pH of the composition of the invention is in the range 7.6 to 7.8.

The added buffer can be a MOPS or TRIS buffer, for example.

The composition contains the compounds of the invention in a concentration in the range 100 µM to 1000 µM.

The compositions and compounds defined in the context of the invention are capable of activating endogenous coagulation in contact with a plasma sample; in other words, they are capable of activating factor XII to factor XIIa, after being brought into contact and incubated with a plasma sample in the presence of PF3 and calcium, at a temperature of about 37° C.

The invention also relates to a system of reagents used for in vitro examination of endogenous coagulation in a blood sample, which system includes a compound or a composition as defined above among its reagents.

A preferred reagent of the invention comprises a salt of gallic acid (gallate) in the activated form, with formula:

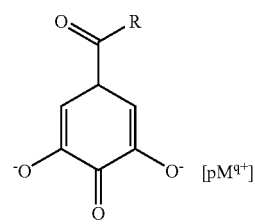

M, q and p having the definitions given above;
R represents $$-\!\!\!-\!\!\!\{\mathrm{O}\!\!-\!\!\{\mathrm{CH_2}\}_m\}_n\!\!-\!\!\mathrm{OH}, \text{ or } -\!\!\!-\!\!\!\{\mathrm{NH}\!\!-\!\!\{\mathrm{CH_2}\}_m\}_n\!\!-\!\!\mathrm{NH_2},$$

m being equal to 2, 3, 4 or 5 and n being a whole number between 1 and 170; or $$-AA_1-AA_2-\ldots -AA_r.$$

AA being a natural or exotic amino acid and r being a whole number between 1 and 10.

In particular, within the context of the definition of R, n is in the range 1 to 50, for example in the range 1 to 30, advantageously in the range 1 to 20.

Particular preferably in the above formulae, n equals 1, 2, 3, 4, 5, 6, 7, 8, 9 or 10.

Determining the Concentrations of the compounds of the invention takes into account the fact that in the APTT system, the expected coagulation times for the plasmas from healthy subjects are generally in the range 28 to 40 seconds. In this context, the concentration of compounds of the invention and the other constituents employed for the coagulation test can be defined from the desired coagulation time for the samples from healthy plasmas. In particular, the concentration of compounds of the invention can be between 100 µM and 1000 µM.

Optimising the concentrations of the principal constituents of the reagent is aimed at producing coagulation times within this interval for a range of plasma samples from at least 30 healthy subjects.

Further, optimising the biochemical parameters around the active principals of the APTT reagent can allow the time to be extended, thereby adjusting the detection sensitivity for certain disorders revealed by the APTT test. Thus, for example, an extension of time with respect to a healthy reference subject of at least 20% is sought in cases of Lupus Anticoagulant Syndromes. For plasmas from subjects treated with non-fractionated heparin anticoagulants, the time extensions range from a ratio of 1.5 to 3.0 times the reference times that are sought. For type A and B haemophilia, the highest possible sensitivity is required and large time extensions are sought.

Preferably, the reagent so constituted comprises activated ethylene glycol gallate. The activity results from the keto-enol equilibrium obtained and its stabilisation at a physiologically acceptable pH.

In a particular embodiment of the invention, the concentration of gallate, in particular ethylene glycol gallate, in the composition or reagent system described is advantageously in the range 100 to 1000 µM, preferably 100 µM.

The invention also relates tout any compound or any composition among those defined above, for the preparation of a reagent for the exploration of the endogenous coagulation, especially for performing an APTT test, wherein said compound or composition is in association with a constituent which has an activity of modulation on the sensitivity of the response of the compound or composition of the invention.

The modulation of the sensitivity can consist in an attenuation of the extension of the coagulation time observed on samples of plasmas from patients affected by a pathology of the type of Lupus Anticoagulants or from patients treated with anticoagulant substances, for example based on non-fractionated heparin anticoagulants.

Alternatively this modulation of the sensitivity can consist in a decrease of the coagulation time measured on non pathological plasma samples.

Such a constituent suitable for modulating the sensitivity of a reagent prepared with the compounds or with the compositions of the invention is a poly-aminoacid, in particular a substituted poly-aminoacid, especially substituted in part, the substitution relating to the amino groups which are substituted with succinyl (—CO—CH2—CH2 COOH) or glutaryl (—OC(CH2)3 CO) groups.

The substitution must not affect the spatial conformation and/or the stability of the original constituent, in such conditions that the substituted poly-aminoacid would no more be capable of achieving its modulation effect on the sensitivity.

For these reasons, a wholly substituted poly-aminoacid would a priori not be convenient.

According to a preferred embodiment of the invention, the modulator constituent is a substituted polylysine, (either D- or L-polylysine or a mixture thereof) especially succinylated, and for example it is substituted L-Polylysine, advantageously succinylated L-Polylysine. The inventors have especially used the succinylated L-Polylysine available in the SIGNMA catalogue (2001-2002). Glutarylated polylysine can also be used.

Advantageously, succinylated L-Polylysine can be used, which has a molecular weight in a range of 20 000 to 300 000 Da, preferably in a range of 50 000 to 300 000 Da.

The concentration of the modulator constituent, in the reagent prepared in order to carry out the APTT test, and in particular the concentration of the succinylated L-Polylysine (SIGMA) is within a range of 10 to 100 µg/ml, preferably in a range of 50 to 100 µg/ml.

The substituted poly-aminoacid, in particular the succinylated polylysine, can be added at any time during the preparation of the reagent for use in a test for the exploration of the endogenous coagulation, such as APTT.

In addition to the contact activator for endogenous coagulation, the reagent system of the invention comprises a substitute for phospholipids in the platelet membrane. This substitute can be cephaline: a suspension of phospholipids extracted from mammalian brains.

The invention also concerns a reagent system also comprising, separate from the other reagents, $Ca^{2+}$ ions to trigger activation of the factors involved in the endogenous pathway.

The reagents of the invention and where appropriate the other constituents used in order to carry out an APTT test, can be arranged in a kit.

The compounds, compositions or reagents of the invention for exploring coagulation and in particular endogenous coagulation can be used to measure the activated partial thromboplastin time (APTT) for a blood sample in particular a plasma sample. In this regard, we advantageously use platelet-depleted plasma.

Within the context of this measurement, the normal conditions for carrying out this test were complied with, in particular regarding sample preparation.

The plasma sample may initially have been treated with citrate, for example, to complex the $Ca^{2+}$ ions contained in the sample so that the sample can no longer coagulate. The sample is then incubated with a compound or a composition of the invention as a coagulation activator and with phospholipid substitutes. $Ca^{2+}$ ions are then added in a quantity equivalent to that which has been complexed, to trigger coagulation.

The activity of the compounds or compositions of the invention requires that their pH is of a physiologically acceptable value.

The compounds, compositions or reagents of the invention can also be used to determine the coagulation time of whole blood or the coagulation time of plasma.

Thus, the invention allows the use of a compound or composition in accordance with the above description, for the preparation of a system of reagents for examining coagulation factors involved in the endogenous coagulation pathway. The factors concerned are principally factors XII, XI, IX and VIII.

In this context, the invention concerns, for example, the detection of anomalies related to Willebrand's disease, to haemophilia A and B or to the detection of anticoagulants. These anomalies result in an APTT time that is outside normal values, which latter are normally between 20 and 40 seconds.

Thus, the invention also concerns a method for measuring the activated partial thromoboplastin time (APTT) comprising the steps of:

bringing a platelet-depleted plasma sample into contact with compounds or compositions in accordance with the invention, in the presence of substitutes for the phospholipids of the platelet membrane, under conditions that allow activation of the endogenous coagulation pathway;

adding $Ca^{2+}$ ions in a quantity equivalent to the quantity of these ions that have been complexed in the plasma sample;

measuring the time required to transform fibrinogen into fibrin.

In particular, within the context of carrying out the above method, the plasma sample is constituted by a platelet-depleted plasma and a coagulation activator is incubated with the plasma for a period of about 2 to 5 minutes, at 37° C. The phospholipid membrane substitutes are either added from the start of the reaction, or mixed with the activator, or added individually during the reaction.

Then the calcium ions are added, for example in the form of calcium chloride in a concentration in the range 20 mM to 25 mM. The time required for fibrin formation is then measured.

When it is outside the time interval corresponding to a normal coagulation situation (i.e., between 20 and 40 seconds), the measured time indicates that one of the parameters of the endogenous coagulation pathway is in an abnormal amount, including being absent, or that anticoagulating compounds exist in the test plasma.

When the test plasma comprises a factor for the endogenous coagulation pathway in an abnormal amount, the invention can then allow quantitative analysis of the factor in question to be carried out, using a system that is depleted in that factor, and in which all the other parameters are introduced in excess. In this system, after adding the plasma to be studied, only the factor to be assayed is in a limiting quantity.

The invention also concerns a process for preparing a compound with the following formula:

(I)

in which:

A represents one or more compounds selected from the following formulae:

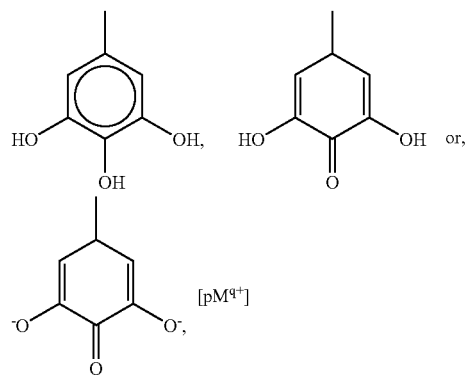

$M^{q+}$ representing a cation, q being equal to 1 or 2 and p being such that p×q=2;

R represents

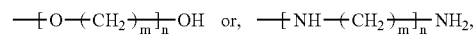

m being equal to 2, 3, 4 or 5 and n being a whole number between 1 and 170; or

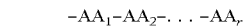

AA being a natural or exotic amino acid and r being a whole number between 1 and 10;

said process comprising the steps of:

esterifying gallic acid in the presence of a compound containing at least one alcohol function, or amidifying gallic acid in the presence of a compound containing at least one amine function;

bringing the gallic acid derivative obtained into contact with $OH^-$ ions to form a compound with formula:

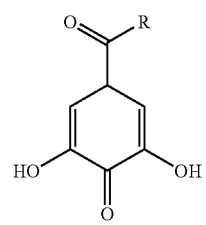

(II)

adding a metal cation $M^{q+}$ (in which q equals 1 or 2) under conditions enabling the formation of a complex with formula:

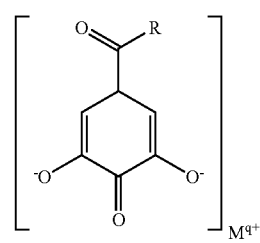

(III)

stabilising the equilibrium obtained between compounds (II) and (III) at a physiologically acceptable pH by adding a buffer such as MOPS or TRICINE;

recovering the solution obtained.

This process is preferably such that esterification is carried out in the presence of ethylene glycol to form ethylene glycol gallate, thereby allowing the recovery, when the reactions are complete, of products of the keto-enol equilibrium particularly comprising the acidic and basic forms of oxidised ethylene glycol gallate and if necessary also a residual quantity of ethylene glycol gallate.

The definition of the process encompasses the definitions of the preferred families or groups of compounds or compositions of the invention.

In a particular embodiment of the invention, it may be desirable to recover principally the basic form of the oxidised ethylene glycol gallate with formula (V) and to this end, it may be advantageous to displace the equilibrium towards this basic form.

A further method has been developed by the inventors for preparing a compound with formula A in accordance with the invention having endogenous coagulation activation properties. This process comprises the steps of:

esterifying gallic acid;
  heating the gallic acid ester obtained to a temperature in the range 70° C. to 90° C., preferably to 80° C. for a period in the range 16 hours to 24 hours, preferably 24 hours, at an alkaline pH in a buffer solution;
  recovering the different forms of gallic acid ester present in solution.

Other properties and advantages of the invention will become apparent from the following examples, which constitute preferred embodiments and implementations of the subject matter of the invention.

EXAMPLE 1

In this example, the coagulation time was measured with APTT reagents produced in accordance with the invention, using a variety of cations. Different types of plasma were tested, both normal and representing diseases revealed by an APTT test:

CK-Prest=reference APTT reagent in which the contact activator is kaolin;
  pool N=mixture of equivalent quantities of plasmas originating from healthy subjects;
  CCN=coag. control normal: control plasma, normal level;
  CCP=coag. control patho: control plasma, disease level;
  heparins=plasmas from a patient receiving an anticoagulating treatment based on non-fractionated heparin in the form of sodium or calcium salts;
  lupus=plasma from a patient presenting with Lupus Anticoagulant Syndrome;
  def f VIIIc=plasma from a patient presenting with a f VIIIc deficit (haemophilia A).

The measurements were carried out using a haemostasis instrument (STA-Diagnostica Stago).

| | Coagulation time, seconds | | | | | | |
|---|---|---|---|---|---|---|---|
| | Control plasma | | | Heparins | | Lupus | F VIII |
| Cations | Pool N 1098 | CCN | CCP | Batch 1635 | Batch 1726 | Batch 021 | def 16% |
| Cu | 36.3 | 41.7 | 69.7 | 45.1 | 57.2 | 63.1 | 50.0 |
| Mn | 37.8 | 34.2 | 54.9 | 73.1 | 51.0 | 63.6 | 52.4 |
| Co | 97.6 | >140.0 | >140.0 | >140.0 | >140.0 | >140.0 | >140.0 |
| Cd | 114.6 | 137.2 | >140.0 | >140.0 | >140.0 | >140.0 | >140.0 |
| Ni | 120.8 | 137.3 | >140.0 | >140.0 | >140.0 | >140.0 | >140.0 |
| Cs | 121.0 | 122.5 | >140.0 | >140.0 | >140.0 | >140.0 | >140.0 |
| Sr | 125.6 | 130.9 | >140.0 | >140.0 | >140.0 | >140.0 | >140.0 |
| Zn | 127.6 | >140.0 | >140.0 | >129.1 | >140.0 | >140.0 | >140.0 |
| Cr | >140.0 | >140.0 | >140.0 | >140.0 | >140.0 | >140.0 | >140.0 |
| Fe | 112.3 | 132.7 | >140.0 | >140.0 | >140.0 | >140.0 | >140.0 |
| Mo | 120.0 | >140.0 | >140.0 | >140.0 | >140.0 | >140.0 | >140.0 |
| Ref: CK-Prest | 30.4 | 30.9 | 52.7 | 60.2 | 130.8 | 45.5 | 45.9 |

EXAMPLE 2

In the next example, the coagulation times for different plasmas were determined from APTT reagents obtained from amides or esters of gallic acid.

normal plasmas=pool of equivalent quantities of plasmas from normal subjects;
  CCN=coag. control normal: control plasma, normal level;
  CCP=coag. control patho: control plasma, disease level;
  heparins=plasmas from patient receiving an anticoagulating treatment based on non-fractionated heparin in the form of sodium or calcium salts;
  lupus=plasma from a patient presenting with Lupus anticoagulant Syndrome;
  def.f VIIIc=plasma from a patient presenting with a f VIIIc deficit (haemophilia A).

| | | | Coagulation time in seconds obtained using an automated haemostasis instrument (STA - Diagnostica Stago) | | | | | |
|---|---|---|---|---|---|---|---|---|
| | | | Normals and controls | | | Heparins | | Lupus | f VII |
| Gallic acid derivatives | | | Pool N | | | Batch | Batch | Batch | def |
| amides | n | [µM] | LIK 800 | CCN | CCP | 1706 | 0811 | 021 | 25% |
| $H_2N-(CH_2)_n-NH_2$ | 2 | 100 | 111.5 | 138.1 | 177.9 | 228.4 | >300.0 | 167.6 | 113.0 |
| | 3 | 100 | 110.9 | 119.3 | 177.9 | 243.9 | >300.0 | 155.8 | 111.3 |
| double amide gallate | 2 | 100 | 148.2 | 170.6 | 203.8 | — | >300.0 | >300.0 | 128.5 |
| $H_2N-CH-(CH_2OH)-COOH$ | — | 100 | 245.0 | 210.9 | 189.3 | — | >300.0 | 232.6 | 153.0 |
| ester | | | | | | | | | |
| $HOCH_2-CH_2-OH$ | | 100 | 37.4 | 32.7 | 50.5 | 65.7 | 112.5 | 45.7 | 35.6 |
| reference | — | — | 33.9 | 33.7 | 49.3 | 66.9 | 61.1 | 35.9 | 40.5 |

It can be seen from this table that the nearest results to those obtained with the reference reagent, CK-Prest, were those obtained with ethylene glycol gallate.

EXAMPLE 3

After heating for 24 hours at 80° C., 500 µM of ethylene glycol gallate in solution buffered to a pH of 7.00 became-active in an APTT coagulation test. The table below shows the molecule's activation kinetics.

The procoagulating activity of the ethylene glycol gallate solution was compared with that of a reference reagent: CK-PREST, an APTT reagent in which the activator is kaolin. The instrument used to measure the coagulation time was an automated STA Diagnostica Stago haemostasis instrument (series n° 307).

In parallel with the appearance of coagulation activity, a yellow colour that was measurable at 355 nm appeared.

The test plasmas were quality control plasmas:

CCN=coag control normal; CCP=coag control patho, batch n° 980901.

APTT reagent produced=ethylene glycol gallate, 500 µM, oxidised at 80° C.+Tricine, 50 nM, pH 7.00+cephaline (substitute for platelet phospholipids).

| Heating time at: | Reference: CK PREST | | APTT - ethylene glycol gallate | | |
|---|---|---|---|---|---|
| T = 80° C. | CCN | CCP | CCN | CCP | OD (355 nm) |
| T0 | — | — | >140.0 | >140.0 | 0.102 |
| T1 h | 34.9 | 49.2 | >140.0 | >140.0 | 0.223 |
| T2 h | 35.3 | 49.1 | >140.0 | >140.0 | 0.356 |
| T3 h | 35.1 | 48.4 | >140.0 | >140.0 | 0.573 |
| T4 h | 34.8 | 49.5 | >140.0 | >140.0 | 0.792 |
| T5 h | 35.0 | 50.1 | 136.9 | 134.8 | 0.966 |
| T6 h | 35.1 | 48.4 | 118.4 | 118.5 | 1.155 |
| T7 h | 35.1 | 48.2 | 108.2 | 110.4 | 1.308 |
| T8 h | 35.7 | 47.8 | 94.9 | 100.2 | 1.458 |
| T9 h | 35.0 | 48.2 | 88.8 | 95.1 | 1.563 |
| T10 h | 35.0 | 48.4 | 81.4 | 87.9 | 1.650 |
| T11 h | 35.3 | 48.3 | 71.3 | 80.7 | 1.754 |
| T12 h | 35.0 | 48.6 | 65.7 | 75.5 | 1.859 |
| T13 h | 34.7 | 48.4 | 61.6 | 71.0 | 1.926 |
| T14 h | 35.1 | 48.8 | 55.0 | 66.3 | 2.028 |
| T26 h | 35.2 | 49.1 | 37.6 | 54.4 | 2.616 |
| T27 h | 35.0 | 49.5 | 36.3 | 53.5 | 2.712 |
| T28 h | 35.0 | 47.9 | 35.6 | 53.7 | 2.720 |
| T30 h | 35.0 | 48.3 | 35.8 | 54.1 | 2.766 |
| T34 h | 35.1 | 49.5 | 34.5 | 52.5 | 2.750 |

EXAMPLE 4

A variety of buffer molecules selected from those routinely used in biological systems could produce, within reasonable heating time periods (<4 days), significant procoagulation activities that were close to those of the reference reagent, CK-PREST. They were the following molecules:

TRICINE: N- tris(hydroxymethyl)methyl glycine;

HEPES: N-2-hydroxyethylpiperazine-N'-2-ethanesulphonic acid;

MOPS: (N-morpholino)propanesulphonic acid;

TRIS: [tris-(hydroxymethyl)aminomethane].

The TRICINE and MOPS buffers are preferably used, as with TRIS, a precipitate appears during activation of the ethylene glycol gallate, and with the HEPES buffer, heating has to be carried out for a longer period. The table below shows the performances obtained for 2 control plasmas (normal and pathological), 1 plasma pool from healthy donors and 4 plasmas representing disorders detectable in an APTT type coagulation system:

pool N=pool of a plurality of normal plasmas;

CCN=coag. control normal: control plasma, normal level;

CCP=coag. control patho: control plasma, pathological level;

LA: plasma from patient presenting with a Lupus Anticoagulant Syndrome;

Hep=plasma from patients receiving an anticoagulating treatment based on non-fractionated heparin in the form of the calcium salt. Two plasmas with 2 levels of heparinaemia were tested: 0.09 and 0.034 International Units per ml;

def.f VIIIc=plasma from haemophilia A with 40% factor VIIIc activity.

The coagulation times obtained are shown in seconds.

The response sensitivity obtained with each of the reagents produced with the 4 buffers was rendered objective by calculating a ratio (R) produced by dividing the coagulation time obtained for the patient's plasma by that obtained with the normal pool, or the pathological coagulation control (CCP) by that of the normal control (CCN).

$$R = \frac{\text{Patient's coagulation time}}{\text{Pool } N \text{ coagulation time}}$$

| | Reference CK-Prest Batch | APTT - ethylene glycol gallate | | | | | | | |
|---|---|---|---|---|---|---|---|---|---|
| | n° 980201 | TRICINE | | HEPES | | MOPS | | TRIS | |
| Plasmas | Sec | Sec | R | Sec | R | Sec | R | Sec | R |
| PN (batch n° 10-98) | 30.5 | 39.4 | — | 35.6 | — | 37.0 | — | 32.3 | — |
| CCN (batch n° 972751) | 31.5 | 38.7 | — | 33.5 | — | 35.4 | — | 31.9 | — |

-continued

| | Reference CK-Prest Batch | | APTT - ethylene glycol gallate | | | | | | |
|---|---|---|---|---|---|---|---|---|---|
| | n° 980201 | | TRICINE | | HEPES | | MOPS | | TRIS |
| Plasmas | Sec | R | Sec | R | Sec | R | Sec | R | Sec | R |
| CCP (batch n° 972751) | 52.3 | 1.66 | 56.8 | 1.47 | 52.0 | 1.46 | 56.5 | 1.60 | 72.1 | 2.26 |
| LA (batch n° MA 221) | 45.6 | 1.50 | 76.3 | 1.94 | 64.6 | 1.81 | 67.7 | 1.83 | 58.8 | 1.82 |
| Hep, (0.09 IU/ml) | 59.6 | 1.95 | 49.5 | 1.26 | 48.7 | 1.37 | 52.5 | 1.42 | 55.2 | 1.71 |
| Hep, (0.34 IU/ml) | 117.4 | 3.85 | 67.1 | 1.70 | 71.7 | 2.01 | 81.4 | 2.20 | 107.3 | 3.32 |
| Def, VIIIc (40%) | 45.9 | 1.50 | 55.1 | 1.40 | 51.0 | 1.43 | 53.4 | 1.44 | 48.3 | 1.50 |

EXAMPLE 5

The use of an APTT reagent can have two aims:
general exploration of the endogenous blood coagulation pathway with a normal-abnormal response;
analytical and quantitative exploration of coagulation factors involved in the endogenous coagulation pathway: f XII-XI-IX-VIIIc;
it is possible to assay, in a patient's plasma, any coagulating factor in the endogenous pathway using a system that is specifically depleted in that factor. All other parameters are introduced in excess; only the factor to be assayed is then in a limiting quantity. Its activity becomes quantifiable after comparison with a calibration curve that has been produced under the same conditions. Depending on the size of the deficit, the coagulation time is extended to a greater or lesser extent (Figure; also, see example for factor VIIIc).

| Coagulation time in seconds obtained using automated haemostasis instrument (STA Diagnostica Stago) | | |
|---|---|---|
| Amount of f VIIIc (%) | Reference: CK PREST batch n° 991621 | APTT - ethylene glycol gallate |
| 0 | 88.2 | 92.9 |
| 12 | 43.4 | 51.1 |
| 23 | 39.4 | 45.8 |
| 35 | 36.8 | 42.3 |
| 47 | 34.7 | 40.3 |
| 59 | 33.6 | 38.8 |
| 70 | 32.6 | 37.8 |
| 82 | 31.6 | 36.3 |
| 94 | 30.6 | 35.4 |
| 105 | 30.0 | 34.7 |
| 117 | 29.7 | 34.0 |

EXAMPLE 6

The coagulating activity of an APTT reagent requires the joint action of two active principles:
a molecule activating the contact phase of the endogenous pathway. In fact, this was ethylene glycol gallate activated by heating to 80° C.;
a substitute for the phospholipids of the platelet membrane, cephaline, obtained by extracting rabbit brains with chloroform;

Optimum activity of the APTT reagent thus constituted depends on the concentrations of ethylene glycol gallate and cephaline.

The following tables show the results obtained for representative plasmas for different disorders and for some controls.

| Ethylene Glycol gallate [μM] | Coagulation time, seconds | | | | | |
|---|---|---|---|---|---|---|
| | Control batch n° 80901 | | Plasma (LA) | Plasmas Batch | Heparins Batch | Plasma def |
| | Normal | Path | MA 030 | 1635 | 1726 | f VIIIc |
| 0 | >140.0 | >140.0 | >140.0 | >140.0 | >140.0 | 117.4 |
| 10 | 130.6 | >140.0 | >140.0 | >140.0 | >140.0 | 121.9 |
| 25 | 124.5 | 103.3 | 103.3 | >140.0 | >140.0 | 73.1 |
| 50 | 88.6 | 99.6 | 66.6 | 73.1 | >140.0 | 44.8 |
| 75 | 46.5 | 67.4 | 50.4 | 48.3 | 86.6 | 38.6 |
| 100 | 38.4 | 46.2 | 47.5 | 48.0 | 80.0 | 38.2 |
| 200 | 35.2 | 42.5 | 46.7 | 48.5 | 75.4 | 37.7 |
| 300 | 34.3 | 39.6 | 44.2 | 47.7 | 73.7 | 37.5 |
| 400 | 32.9 | 39.6 | 43.4 | 47.0 | 75.1 | 37.2 |
| 500 | 32.6 | 48.5 | 43.0 | 47.3 | 76.1 | 37.5 |
| 1000 | 33.4 | 51.5 | 42.5 | 47.9 | 76.3 | 37.1 |
| CK Prest batch n° 981201 | 34.2 | 47.6 | 38.3 | 57.1 | 121.5 | 38.9 |

The choice can be made between concentrations in the range 100 μM to 1000 μM. Our preference is a concentration of 100 μM.

Determination of optimum cephaline concentration.

| Coagulation time, seconds, using automated haemostasis instrument (STA Diagnostica Stago) | | | | |
|---|---|---|---|---|
| Cephaline Dilutions of starting material | Normal pl. pool Batch 05-99 | LA batch n° MA 2623 | Plasma, heparin Batch n° 1680 | f VIIIc deficient plasma Batch GK903901 |
| 1:200 | 44.8 | 106.7 | 64.5 | 60.0 |
| 1:100 | 39.7 | 79.7 | 60.3 | 54.7 |
| 1:50 | 36.9 | 52.0 | 59.4 | 52.1 |
| 1:40 | 36.4 | 48.3 | 59.0 | 51.1 |
| 1.5:50 | 37.1 | 45.4 | 59.3 | 51.5 |
| 1:30 | 37.1 | 43.1 | 60.5 | 52.2 |
| 1:20 | 38.3 | 41.8 | 66.3 | 54.0 |
| CK Prest batch n° 981201 | 33.0 | 38.6 | 84.8 | 49.5 |

EXAMPLE 7

Selecting Concentration of Manganese Chloride

In this example, the coagulation time was measured with APTT reagents produced in accordance with the invention, and for which the concentration of manganese chloride was varied.

The test plasmas were quality control plasmas. Two levels were used: a normal level and a pathological level.

The commercial CK Prest reagent was tested in parallel and constituted the reference.

| Coagulation time in seconds, obtained using automated haemostasis instrument (STA Diagnostica Stago) | | | | | | |
|---|---|---|---|---|---|---|
| Plasma samples | Concentration of $MnCL_2$ [µM] | | | | | CK Prest (reference time) |
| | 0 | 1 | 2 | 10 | 20 | |
| Normal control | 144.2 | 50.8 | 40.7 | 34.8 | 41.6 | 31.8 |
| Path. Control | 125.9 | 51.6 | 48.2 | 49.5 | 56.1 | 49.7 |

Preferably, a concentration of 10 µM is employed.

EXAMPLE 8

It may be advantageous to be able to modulate the sensitivity of the response of an APTT reagent with respect to certain anomalies of the coagulation time observed in various pathological situations. This modulation aims at obtaining a reagent which has specific features as far as the sensitivity of the response is concerned, which features are reproducible from one production lot to another.

The inventors have observed that when addition was made, of succinylated L-Polylysine (SIGMA) in the APTT reagent containing ethylene glycol gallate, it was possible to lessen the coagulation time which could be obtained on plasmas obtained from patients presenting a Lupus Anticoagulants Syndrome or from patients treated with anticoagulants based on non-fractionated heparin. Also, it has been observed that the use of succinylated L-Polylysine allows to decrease the coagulation time measured on plasmas obtained from a normal population.

These observations can be obtained through the use of a poly-aminoacid more or less substituted at the level of the amino groups, with succinyl or glutaryl groups, in order to define the level of sensitivity of the reagent.

One of the preferred embodiments of the invention consists in using partially substituted L-Polylysine. The following tables summarize the results obtained on various control plasmas used within the examples.

CCN: Coag Control Normal
CCP: Coag Control Pathological
Pool N: Pool of a plurality of normal plasma
LA: plasma from patient presenting a Lupus Anticoagulant Syndrome
Heparin: plasma from patients receiving an anticoagulant treatment based on non-fractionated heparin.
Def VIII C: plasma from haemophilia A with 40% factor VIII activity.

| coagulation time in secondes on a STA Diagnostica Stago automate apparatus | | | | | |
|---|---|---|---|---|---|
| Succinylated L-Polylysine-molecular weight: 20 000–30 000 | | | | | CK Prest |
| [µg/ml] | 0.0 | 5.0 | 7.5 | 10.0 | Reference |
| CCN | 32.9 | 32.0 | 32.4 | 37.3 | 33.3 |
| CCP | 56.1 | 51.7 | 49.2 | 53.5 | 49.9 |
| Pool N | 38.2 | 35.8 | 34.9 | 34.5 | 34.1 |
| LA 1 | 44.7 | 44.1 | 45.2 | 49.0 | 34.2 |
| Heparin 1 | 153.7 | 105.2 | 92.7 | 94.3 | 89.6 |
| Def. F.VIII: C | 50.2 | 51.1 | 52.0 | 54.2 | 40.5 |

| coagulation time in secondes on a STA Diagnostica Stago automate apparatus | | | | | |
|---|---|---|---|---|---|
| Succinylated L-Polylysine-molecular weight: 50 000–300 000 | | | | | CK Prest |
| [µg/ml] | 0.0 | 7.5 | 50 | 100 | reference |
| CCN | 34.5 | 32.3 | 30.7 | 30.1 | 32.6 |
| CCP | 55.2 | 54.0 | 52.9 | 53.4 | 48.2 |
| Pool N | 40.5 | 38.6 | 36.5 | 36.7 | 35.0 |
| LA 2 | 57.7 | 51.3 | 50.1 | 51.6 | 56.2 |
| Heparin 2 | 102.6 | 90.9 | 87.6 | 87.8 | 62.0 |
| Def. F.VIII: C | 51.1 | 50.0 | 46.8 | 47.1 | 39.8 |

For the use of succinylated L-Polylysine within the frame of the invention, the molecular weight of succinylated L-Polylysine is preferably within the range of 50 000 to 300

000 Da and the concentration is preferably for this range of molecular weight from 50 µg/ml.

The invention claimed is:

1. A composition, which comprises a mixture of at least two different compounds with formula:

  (I)

wherein group A and group R are identical or different on said two different compounds, and wherein A is selected from the group consisting of

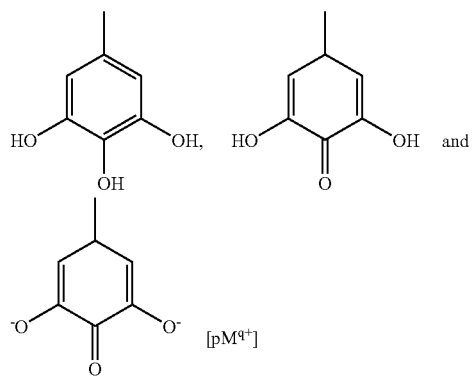

where $M^+$ is a cation, q is 1 or 2 and p×q=2; and wherein R is selected from the group consisting of —[O—(CH$_2$)$_m$]$_n$—OH, where m is equal to 2, 3, 4 or 5 and n is a whole number between 1 and 170, —[NH—(CH$_2$)$_m$]$_n$—NH$_2$, where m is equal to 2, 3, 4 or 5 and n is a whole number between 1 and 170, and a peptide containing between 1 and 12 amino acids, the composition comprising at least a compound wherein A is

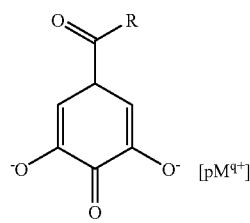  (III)

where $M^+$ is a cation, q is 1 or 2 and p×q is 2.

2. The composition according to claim 1, which comprises a mixture of compounds

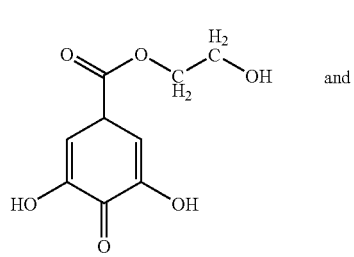  (IV)

and

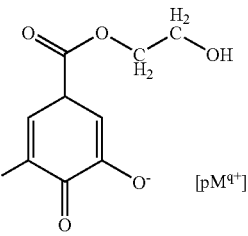  (V)

in which $M^+$ is a cation, q is 1 or 2 and p×q=2, having the acidic and basic forms of oxidized ethylene glycol gallate (EGGox).

3. The composition according to claim 1, which comprises different forms of ethylene glycol gallate produced by the keto-enol equilibrium and having the formula:

  (I)

in which A is selected from group consisting of

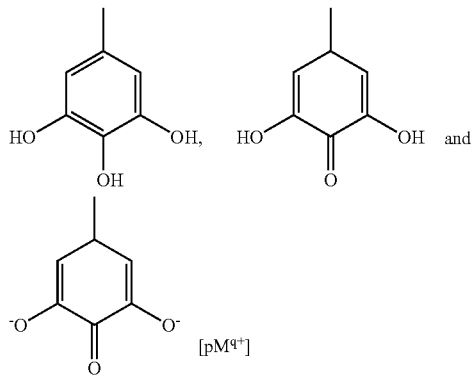

$M^+$ is a cation, q is 1 or 2 and p×q=2; and wherein R is O—CH$_2$—CH$_2$—OH.

4. The composition according to claim 1, which comprises basic EGGox with the formula:

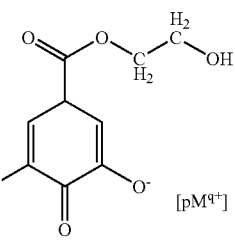  (V)

wherein $M^+$ is a cation, q is 1 or 2 and p×q=2.

5. The composition according to claim 1, which further comprises, in a stabilized equilibrium, compounds with formulae

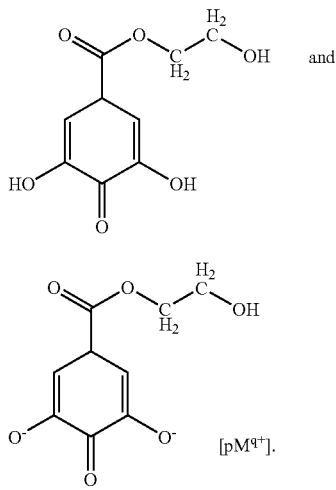

(IV)

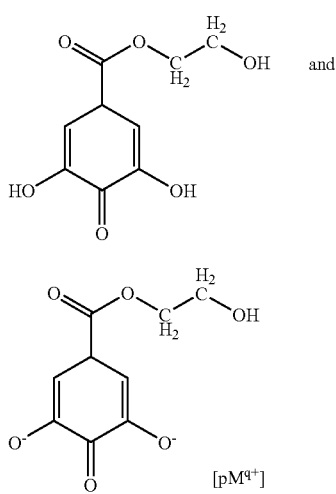

(V)

6. The composition according to claim 1, which contains a mixture of compounds with formulae

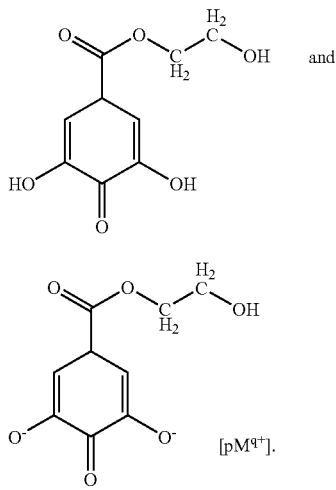

(IV)

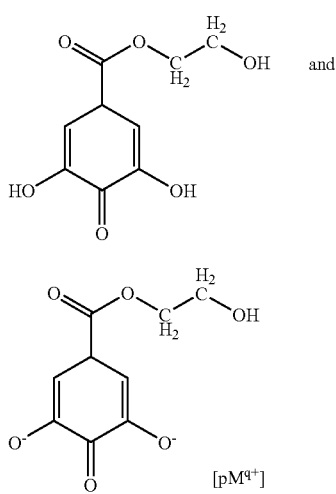

(V)

which pH is in the range of 7.6 to 7.8.

7. The composition according to claim 1, which activates endogenous coagulation in contact with a plasma sample, and which further comprises a buffer selected from from (N-morpholino) propanesulphonic acid (MOPS) or N-tris (hydroxymethyl) methyl-glycine (TRICINE).

8. The composition according to claim 7, wherein the concentration of said compounds is sufficient to activate endogenous coagulation in a plasma sample when contacted with said sample.

9. The composition according to claim 1, wherein the cation is a metal cation.

10. The compound according to claim 9, wherein the metal cation is selected from the group of $Mn^{2+}$, $Cu^{2+}$ or $Co^{2+}$.

11. A reagent system for use in vitro examination of endogenous coagulation, comprising a composition according to claim 1, under conditions such that it constitutes a compound with formula:

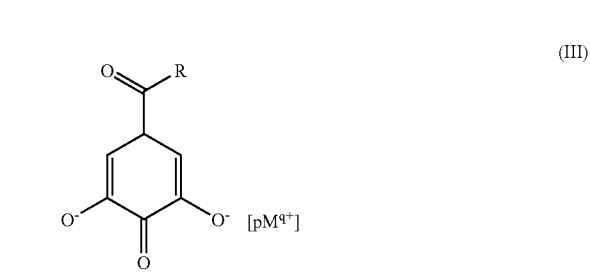

(III)

wherein $M^+$ is a cation, q is 1 or 2 and p×q=2; and wherein R is selected from the group consisting of $-[-(CH_2)_m]_n-$OH, where m is equal to 2, 3, 4 or 5 and n is a whole number between 1 and 170, $-[NH-(CH_2)_m]_n-NH_2$, where m is equal to 2, 3, 4 or 5 and n is a whole number between 1 and 170, and a peptide containing between 1 and 10 amino acids.

12. The composition according to claim 1, or a reagent system according to claim 11, wherein the ethylene glycol gallate concentration is in the range 100 µM to 1000 µM.

13. The composition according to claim 1, further comprising a substituted poly-aminoacid constituent.

14. A process for exploring coagulation by an endogenous pathway comprising measuring an activated thromboplastin time in a blood or a plasma sample using the composition of claim 1.

15. A process for exploring coagulation by an endogenous pathway comprising measuring an activated thromboplastin time in a blood or a plasma sample using the composition of claim 2.

16. A process for exploring coagulation by an endogenous pathway comprising measuring an activated thromboplastin time in a blood or a plasma sample using the composition of claim 13.

17. The composition according to claim 1, wherein n is a whole number between 1 and 50, 1 and 30 or 1 and 20.

* * * * *

UNITED STATES PATENT AND TRADEMARK OFFICE
CERTIFICATE OF CORRECTION

PATENT NO. : 7,208,266 B2 Page 1 of 1
APPLICATION NO. : 10/302649
DATED : April 24, 2007
INVENTOR(S) : Jean-Paul Roisin, Stéphane Steurs and Gérard Quentin It is certified that error appears in the above-identified patent and that said Letters Patent is hereby corrected as shown below:

Column 1, line 11, before "Coagulation" insert --The figure is a graph depicting the use of APTT reagent and blood coagulation.--
Column 12, line 61, "Concentrations" should read --concentrations--.
Column 25, line 42, delete

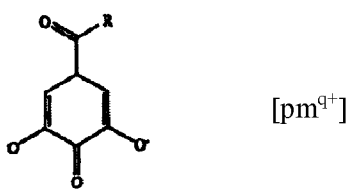 $[pm^{q+}]$ and insert therefor

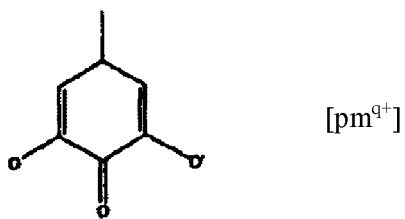 $[pm^{q+}]$

Column 28, line 28, "—[— (CH$_2$)" should read -- —[O—(CH$_2$) --.
Column 28, line 30, "$NH^2$" should read --$NH^2$--.

Signed and Sealed this

Twenty Second Day of April, 2008

JON W. DUDAS
*Director of the United States Patent and Trademark Office*